United States Patent [19]

Doles et al.

[11] Patent Number: 5,436,719
[45] Date of Patent: Jul. 25, 1995

[54] FIBER OPTIC FLAW DETECTOR SYSTEM AND CALIBRATION APPARATUS

[75] Inventors: Joseph E. Doles, Franklin; Robert J. Hadick, Centerville, both of Ohio

[73] Assignee: LaserMike, Inc., Dayton, Ohio

[21] Appl. No.: 147,930

[22] Filed: Nov. 5, 1993

[51] Int. Cl.⁶ .............................................. G01N 21/89
[52] U.S. Cl. .................... 356/73.1; 356/243; 356/430
[58] Field of Search .............. 356/73.1, 243, 239, 356/430; 359/509

[56] References Cited

U.S. PATENT DOCUMENTS

| | | | |
|---|---|---|---|
| 4,021,217 | 5/1977 | Bondybey et al. | 65/13 |
| 4,131,365 | 12/1978 | Pryor | 356/356 |
| 4,208,126 | 6/1980 | Cheo et al. | 356/51 |
| 4,360,270 | 11/1982 | Jeck | 356/243 |
| 4,363,827 | 12/1982 | Eichenbaum | 427/8 |
| 4,638,168 | 1/1987 | Marino et al. | 250/560 |
| 4,638,169 | 1/1987 | Thomann | 250/560 |
| 4,650,322 | 3/1987 | Fejer et al. | 356/73.1 |
| 4,659,937 | 4/1987 | Cielo et al. | 250/560 |
| 4,852,497 | 11/1989 | Inoue et al. | 250/560 |
| 4,924,006 | 5/1990 | Bailey et al. | 356/73.1 |
| 5,007,738 | 4/1991 | Grant | 356/243 X |
| 5,015,867 | 5/1991 | Siegel et al. | 250/560 |
| 5,083,865 | 1/1992 | Kinney et al. | 359/509 X |
| 5,185,636 | 2/1993 | Button et al. | 356/73.1 |
| 5,208,645 | 5/1993 | Inoue et al. | 356/73.1 |
| 5,216,486 | 6/1993 | Sulleist et al. | 356/385 |
| 5,251,001 | 10/1993 | Dave et al. | 356/73.1 |

OTHER PUBLICATIONS

Presby, H. M., "Refractive index and diameter measurement of unclad optical fibers", *Jou of the Optical Society of America*, vol. 64, No. 3, Mar. 1974, pp. 280–284.

Watkins, L. S. "Scattering from side–illuminated clad glass fibers for determination of fiber parameters", *Journal of the Optical Society of America*, vol. 64, No. 6, Jun. 1974, pp. 767–772.

*Primary Examiner*—Vincent P. McGraw
*Attorney, Agent, or Firm*—Killworth, Gottman, Hagan & Schaeff

[57] ABSTRACT

A system for detecting flaws in an optical fiber includes a light source which generates a beam of collimated light rays to illuminate the optical fiber substantially orthogonal to a longitudinal axis thereof. The beam is scattered by a flaw-free optical fiber into an in-plane scattered segment which is scattered in a radial plane substantially perpendicular to the longitudinal axis of the optical fiber. A flaw in the optical fiber scatters the light rays into an out-of-plane scattered segment which are scattered outside of the radial plane. A light attenuator removes the in-plane scattered segment of the beam and a light detector detects the remaining out-of-plane scattered segment. An electrical circuit monitors the light detected by the light detector and determines whether a flaw is present in the optical fiber. To compensate for fluctuations in the power output of the light source, a linear light detector replaces the light attenuator to detect the in-plane scattered segment of the beam. The total detected light is then used to compensate for fluctuations in the power output of the light source. An apparatus for calibrating the system is also provided which includes an optical test fiber having a known flaw mounted in a cartridge. The cartridge is removeably mounted in a moveable carriage such that the known flaw can be passed into and out of the beam to calibrate the system.

20 Claims, 4 Drawing Sheets

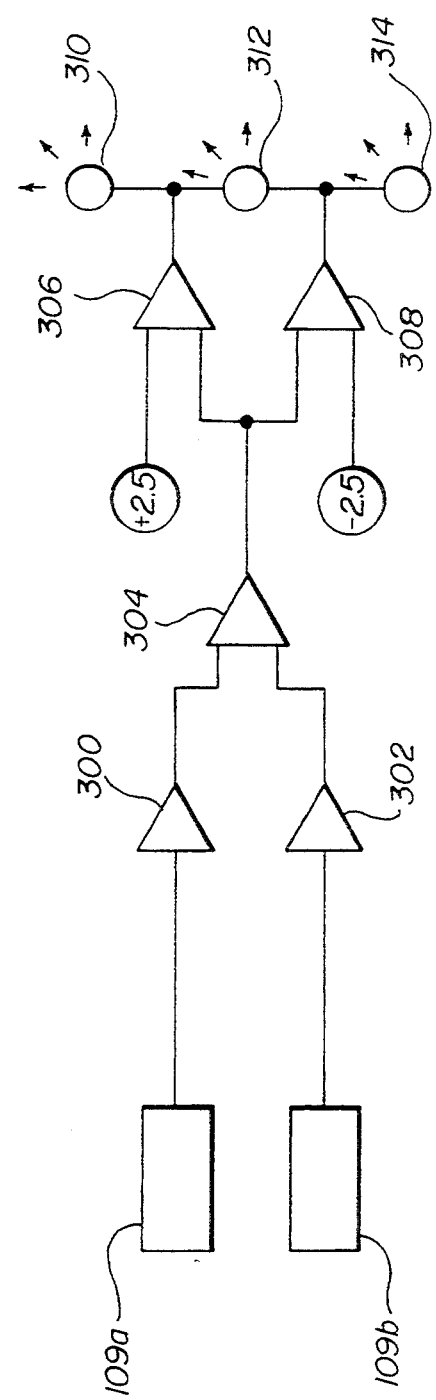
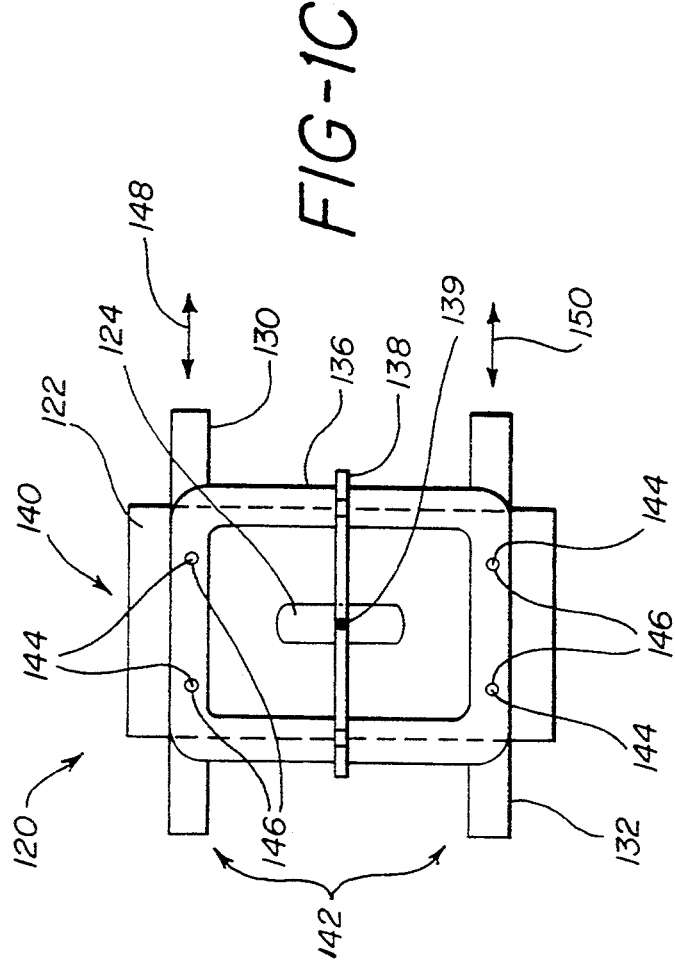

FIBER OPTIC FLAW DETECTOR SYSTEM AND CALIBRATION APPARATUS

BACKGROUND OF THE INVENTION

The present invention relates generally to detecting flaws in optical fibers and, more particularly, to a system for detecting flaws in an optical fiber wherein a laser beam is directed upon the optical fiber in a direction substantially orthogonal to the fiber axis and the portion of the laser beam which is scattered outside of a radial plane substantially perpendicular to the longitudinal axis of the optical fiber by beam flaws is monitored to detect those flaws. An apparatus for calibrating the detector is provided which comprises a movable cartridge containing an optical fiber sample having a known flaw. The cartridge is translated in the laser beam and the detector is adjusted to respond to the scattering of the laser beam by the known flaw.

Due to their excellent transmission characteristics, optical fibers are being increasingly used as signal carriers not only in communication systems but also in a wide variety of other applications including weapon systems and medical diagnostic instruments. Generally, optical fibers consist of a fiber core surrounded by a fiber cladding which has a lower index of refraction than the fiber core. Within the layers of an optical fiber, nonuniformities may occur as a result of the faulty fabrication or improper handling of the fiber. The nonuniformities may include, for example, bubbles, lumps, neckdowns, coating defects, surface contamination, core contamination and the like.

Such nonuniformities may increase the signal losses in the fiber or, in the extreme, completely terminate signal transmission. It is apparent that these deleterious effects of defects or flaws in the optical fiber may result in malfunction of a device in which the fiber is employed. Consequently, optical fibers must be carefully examined to detect any such defects or flaws.

Fiber optic flaw detection systems which direct a laser beam toward an optical fiber and monitor the refraction and diffraction of the laser beam to detect flaws are known in the art. For example, U.S. Pat. No. 4,924,087 issued to Bailey et al. discloses a fiber optic defect detection system wherein the optical fiber to be examined is extended axially through a dish-like structure and illuminated by one or more laser beams directed substantially orthogonal to the fiber axis. For a flaw free optical fiber, the laser beam is scattered by the optical fiber onto a light-absorbing band on an inner surface of the dish as in-plane scattered rays. For an optical fiber having a flaw, a portion of the laser beam is scattered outside the band as out-of-plane scattered rays. Out-of-plane rays which deviate a sufficient amount from the band illuminate an aperture located above the band and are detected as flaws.

Unfortunately, the Bailey et al. flaw detector does not respond to out-of-plane light rays which are scattered below the light-absorbing band such that this detector is at best not as sensitive as possible when detecting flaws which only cause such scattering or predominately scatter rays in that direction. Accordingly, a need still exists in the art for an improved approach to flaw detection in optical fibers which is fast and reliable, accurately detects flaws, is easy to operate and is easily and accurately calibrated.

SUMMARY OF THE INVENTION

This need is met by the fiber optic flaw detector system and apparatus for calibrating the system of the present invention wherein a beam of collimated light rays illuminate an optical fiber substantially orthogonal to a longitudinal axis of the fiber. The light rays are diffracted by the optical fiber into an in-plane scattered segment and, when a flaw is present, into an out-of-plane scattered segment. The in-plane scattered segment is removed by a spatial filter and the remaining out-of-plane scattered segment is monitored to detect flaws in the optical fiber. Alternatively, the in-plane scattered segment may be detected by a linear light detector. The intensity of the in-plane scattered segment and the out-of-plane scattered segment provide an indication of the total power of the beam. This detected total beam power can then be used to compensate for attenuation of the light beam for example as the system ages.

An apparatus for calibrating the system is provided wherein a known flaw contained in an optical test fiber is passed into and out of the beam. The optical test fiber is mounted in a cartridge which is, in turn, mounted on a moveable carriage. The moveable carriage translates in a manner such that the flaw passes into and out of the beam. The system is calibrated by an operator in response to the known flaw.

In accordance with one aspect of the present invention, a system for detecting flaws in an optical fiber includes a light source, which may be a laser beam generator such as a laser diode, for generating a beam of collimated light rays. A first portion of the beam illuminates the optical fiber substantially orthogonal to a longitudinal axis thereof and a second portion of the beam passes around the optical fiber. The first portion of the beam is scattered by the optical fiber into an in-plane scattered segment consisting of light rays which are scattered in a radial plane substantially perpendicular to the longitudinal axis of the optical fiber and an out-of-plane scattered segment consisting of light rays which are scattered out of the radial plane. The out-of-plane scattered segment is the result of flaws in the optical fiber.

A light attenuator is provided for removing the in-plane scattered segment and the second portion of the beam. Preferably, the light attenuator has first and second ends with positioning means mounted thereon. The light attenuator may comprise a spatial filter for removing the in-plane scattered segment of the beam. A first lens assembly, such as a planoconvex lens, focuses the second portion and the in-plane scattered segment of the beam onto the light attenuator.

A light detector, which is preferably a photodetector, detects the out-of-plane scattered segment of the beam and produces a flaw signal representative thereof. The light detector may further comprise a bandpass optical filter for filtering ambient ultraviolet light. The bandpass optical filter is positioned to receive the out-of-plane scattered segment of the beam prior to receipt by the photodetector. In response to the flaw signal, an electrical circuit determines whether a flaw is present in the optical fiber.

Preferably, the fiber optic flaw detector system further comprises a lens cleaner for providing a stream of air over the plano-convex lens to substantially continuously clean the plano-convex lens. The lens cleaner may comprise an air wipe plate adjacent the plano-convex lens for defining an air passage between the plate and the plano-convex lens. The air wipe plate defines an aperture for transmitting the in-plane and out-of-plane scattered segments of the beam. An air source is provided for producing air flow in the air passage to clean the planoconvex lens.

A second lens assembly may be provided to focus the out-of-plane scattered segment of the beam onto the bandpass optical filter and the photodetector. Preferably, the electrical circuit comprises a reference circuit for setting at least one reference signal based on the flaw signal. A comparison circuit compares the flaw signal and the at least one reference signal to determine whether a flaw is present in the optical fiber and generates at least one comparison signal representative thereof. An indicator circuit indicates whether a flaw is present in the optical fiber in response to the at least one comparison signal.

The fiber optic flaw detector system may further comprise positioning means for detecting the beam at the first and second ends of the light attenuator to determine the position of the optical fiber based on the beam and for indicating the position of the optical fiber. Preferably, the positioning means includes first and second photocells positioned on the first and second ends, respectively, of the light attenuator. First and second photocells generate respective first and second position signals representative of the intensity of the light incident thereon. A position circuit determines the position of the optical fiber based on the first and second position signals and provides an indication of the position of the optical fiber.

In accordance with another aspect of the present invention, a system for detecting flaws in an optical fiber has laser beam generating means for generating a laser beam of collimated light rays which illuminate the optical fiber substantially orthogonal to a longitudinal axis thereof. The optical fiber scatters the laser beam into an in-plane scattered segment consisting of light rays which are scattered in a radial plane substantially perpendicular to the longitudinal axis and an out-of-plane scattered segment consisting of light rays which are scattered out of the radial plane. The out-of-plane scattered segment are caused by flaws in the optical fiber.

A linear light detector detects the in-plane scattered segment of the laser beam and generates an in-plane signal representative thereof. The out-of-plane scattered segment is detected by light detection means, such as a photodetector and bandpass optical filter. The light detection means produces a flaw signal representative of the out-of-plane scattered segment. Circuit means determines whether a flaw is present in the optical fiber in response to the flaw signal and the in-plane signal.

A laser lens assembly preferably focuses the laser beam onto the optical fiber. The light detection means may comprise a photodetector and a detector lens assembly for focusing the out-of-plane scattered segment of the laser beam onto the photodetector.

The circuit means preferably comprises a compensation circuit for generating a compensation signal representative of any fluctuation in the power of the laser beam based on the flaw signal and the in-plane signal. Reference means sets at least one reference signal and modulates the at least one reference signal based on the compensation signal. The flaw signal and the at least one reference signal are compared by comparison means to determine whether a flaw is present in the optical fiber. At least one comparison signal is generated by the comparison means representative of the aforesaid comparison. Indication means may be provided for indicating the presence of the flaw in the optical fiber in response to the at least one comparison signal.

In accordance with yet another aspect of the present invention, an apparatus for calibrating a fiber optic flaw detector system which illuminates an optical fiber with a laser beam and includes a detection circuit for detecting scattering of the laser beam by the optical fiber to determine whether a flaw is present in the optical fiber is provided. The apparatus comprises a cartridge with an optical test fiber having a known flaw mounted thereon. Mounting means mounted on the flaw detector system includes a moveable carriage for removeably mounting the cartridge on the mounting means. The moveable carriage is adapted to translate such that the known flaw of the optical test fiber passes into and out of the laser beam to calibrate the fiber optic flaw detector system.

Preferably, the moveable carriage, which may comprise a pair of ball slide assemblies, includes a plurality of mounting pins. The cartridge defines a plurality of mounting apertures each of which is adapted to receive a corresponding one of the plurality of mounting pins to removeably mount the cartridge on the moveable carriage.

These and other features and advantages of the present invention will become apparent from the following detailed description, the accompanying drawings and the appended claims.

BRIEF DESCRIPTION OF THE DRAWINGS

FIG. 1C is a plan view of the light receiving side of the fiber optic flaw detector system of FIG. 1 taken along view line A—A showing an apparatus for calibrating the system;

FIG. 3 is a schematic block diagram of a positioning circuit for determining the position of the optical fiber in the fiber optic flaw detector system of FIG. 1;

DETAILED DESCRIPTION OF THE INVENTION

Figure 1:
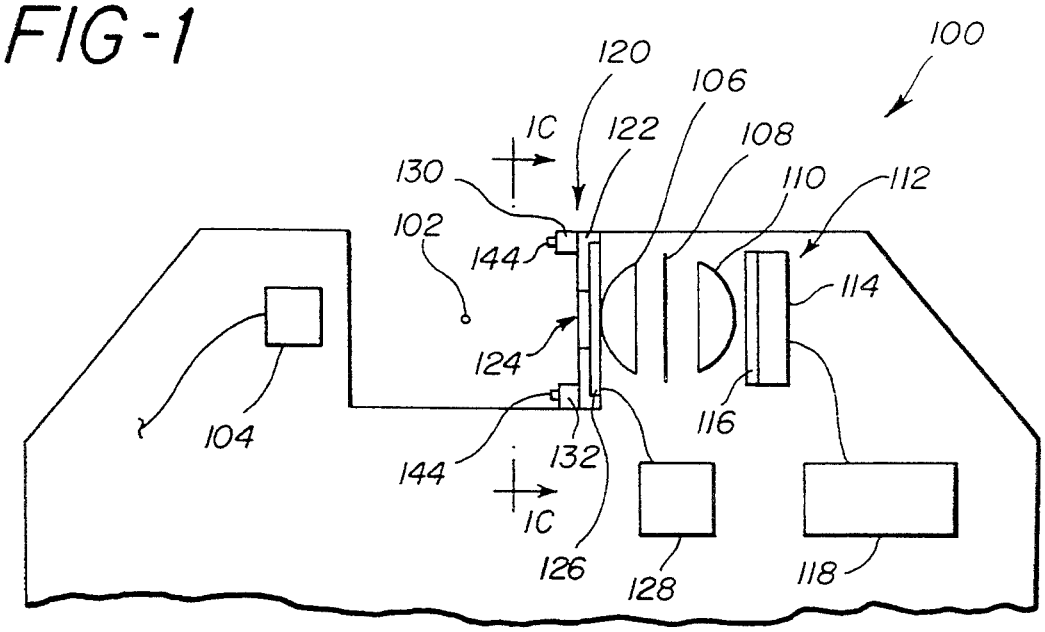
FIG. 1 is a schematic cross-sectional side view of a system for detecting flaws in an optical fiber in which a beam of collimated light rays illuminates an optical fiber in accordance with one embodiment of the present invention.

A system 100 for detecting flaws in an optical fiber 102 includes a light source 104 which generates a beam of collimated light rays. The light rays illuminate the optical fiber 102 substantially orthogonal to a longitudinal axis of the fiber 102. The light source 104 may be a laser beam generator, such as a laser diode. A first lens assembly, shown as a planoconvex lens 106, receives the beam and focuses a portion of the beam onto a light attenuator, such as a spatial filter 108. The spatial filter 108 has first and second photocells 109a and 109b mounted on first and second ends thereof. The photocells 109a and 109b comprise positioning means for determining the position of the optical fiber 102 in the system 100. The positioning means will be described in greater detail below with reference to FIG. 3.

The remaining portion of the beam is focused by a second lens assembly, shown as plano-convex lens 110, onto a light detector 112 which generates a flaw signal representative of the intensity of the remaining beam portion. Preferably, the light detector 112 comprises a photodetector 114 and a bandpass optical filter 116. The optical filter 116 filters ambient ultraviolet light, which may cause erroneous flaw detection, from the remaining portion of the beam before detection by the photodetector 114. An electrical circuit 118 receives the flaw signal generated by the light detector 112 and determines whether a flaw is present in the optical fiber 102.

A lens cleaner, generally designated by reference numeral 120, provides a stream of air over the plano-convex lens 106. The stream of air keeps the plano-convex lens 106 substantially clear of dust and other debris which may inhibit the operation of the system 100. The lens cleaner 120 preferably comprises an air wipe plate 122 adjacent to the plano-convex lens 106. As shown in FIG. 1C, the air wipe plate 122 defines an aperture 124 which permits the beam of collimated light rays to pass through to the plano-convex lens 106.

The air wipe plate 122 further defines an air passage 126 between the plate 122 and the lens 106. A conventional air source (not shown) produces an air flow in the air passage 126 with the air exiting through the aperture 124. A pair of ball slide assemblies 130 and 132 are mounted on the air wipe plate 122 for calibration purposes. The apparatus for calibrating the system 100, including the ball slide assemblies 130 and 132, will be more fully described below.

The path of the beam of collimated light rays in the system 100 will now be described with reference to FIGS. 1A and 1B. The beam, which preferably has an elliptical cross-sectional area having a long axis of approximately 6 mm and a short axis of approximately 2 mm, emanates from the light source 104 and a first portion of the beam illuminates the optical fiber 102. The remaining portion, or second portion, of the beam passes around the optical fiber 102. The first portion of the beam is scattered by the optical fiber 102 into an in-plane scattered segment, generally outlined by dash-dot lines 150, and an out-of-plane scattered segment, generally outlined by dashed lines 152. The in-plane scattered segment 150 is generally contained in a radial plane substantially perpendicular to the longitudinal axis of the optical fiber 102. This radial plane is essentially the plane formed by light rays diffracted by an optical fiber free of flaws.

Both the second portion, the in-plane scattered segment 150 and the out-of plane scattered segment 152 of the beam are focused by the plano-convex lens 106. The plano-convex lens 106 is designed to focus the in-plane scattered segment 150 and the second portion of the beam onto the spatial filter 108 which substantially removes the in-plane scattered segment 150 and the second portion of the beam. Consequently, only the out-of-plane scattered segment 152 of the beam impinges on the photodetector 114. The photodetector 114 generates the flaw signal in response to the out-of-plane scattered segment 152 of the beam in a well known manner.

Figure 2:
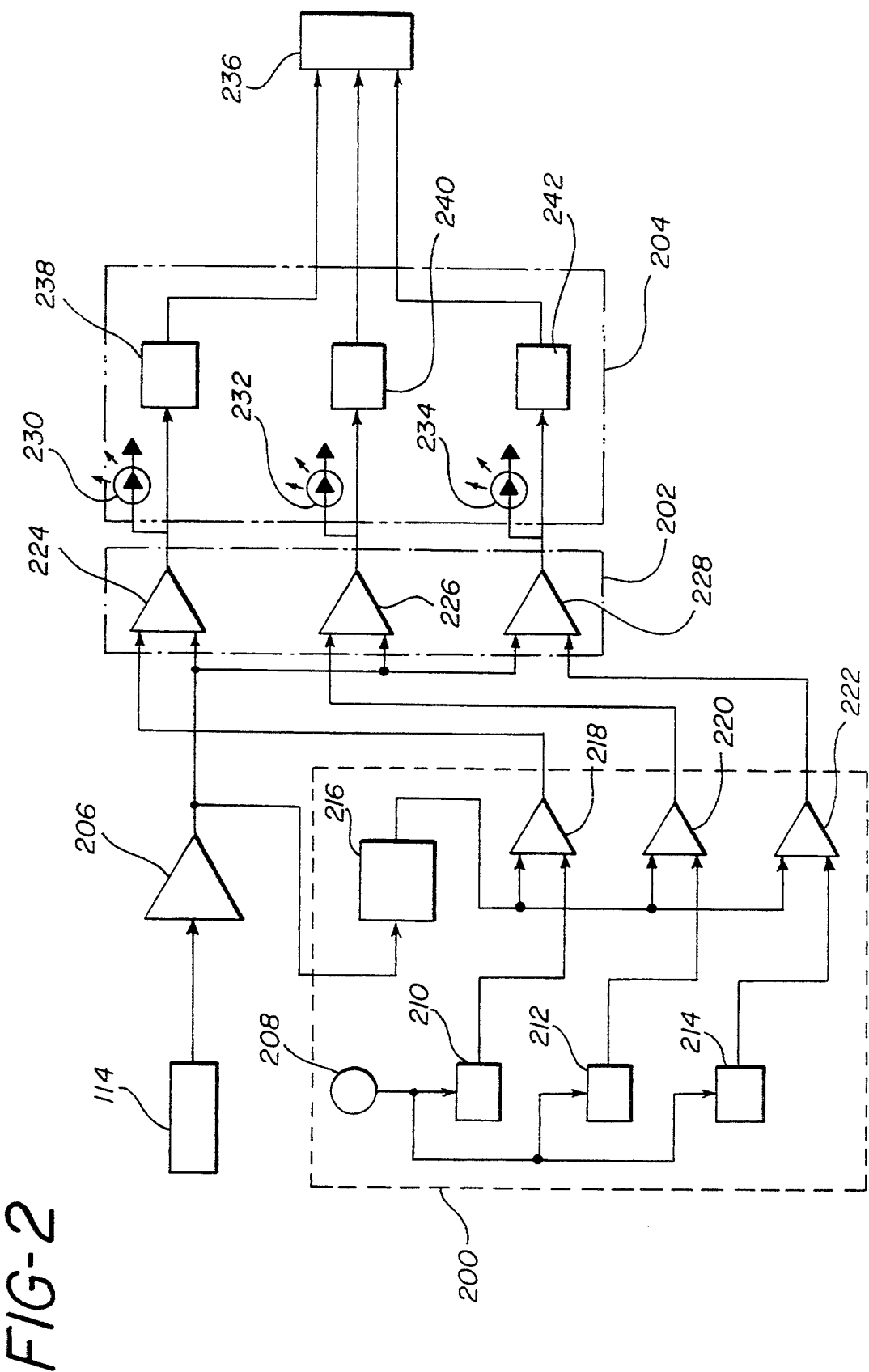
FIG. 2 is a schematic block diagram of an electrical circuit for determining the presence of a flaw using the fiber optic flaw detector system of FIG. 1.

The electrical circuit 118 receives the flaw signal from the detector 114 and determines whether a flaw is present in the optical fiber 102. As shown in FIG. 2, the electrical circuit 118 consists of a reference circuit 200 for setting at least one reference voltage signal, a comparison circuit 202 for comparing the flaw signal with the reference voltage signal to determine whether a flaw is present in the optical fiber 102 and an indicator circuit 204 for indicating whether a flaw is present in the optical fiber 102. It should be understood that although the various circuits are shown in schematic block form in FIG. 2, one skilled in the art will be readily able to manufacture the circuits using conventional electronic circuit elements. Consequently, the individual circuit elements are not hereinafter discussed.

The flaw signal is inverted and amplified by an inverting circuit, shown as an inverting amplifier 206, before being received by the reference circuit 200 and the comparison circuit 202. The reference circuit 200 comprises a reference voltage source 208, one or more threshold potentiometers 210, 212 and 214, a peak voltage detector 216 and one or more summer circuits 218, 220 and 222. The threshold potentiometers 210, 212 and 214 adjust the reference voltage supplied to the respective summer circuits 218, 220 and 222 such that the system 100 can be adjusted to detect different sized flaws.

During operation, the inverted flaw signal will normally be maintained at an average negative value. This average negative value essentially represents the value of the flaw signal for a flaw-free optical fiber. When a flaw is present in the beam of collimated light rays, the flaw signal experiences a positive peak spike since more of the light rays are diffracted into the out-of-plane scattered segment of the beam. However, when inverted by the inverting amplifier 206, this positive peak spike becomes a negative peak spike which is less than the average negative value. The output of the peak voltage detector 216 is maintained at a level consummate with the average negative value and ignores negative peak spikes. Consequently, the peak voltage detector 216 provides compensation for fluctuations in the output power of the laser source by following fluctuations in the average value of the flaw signal.

The output of the peak voltage detector 216 is then added to the reference voltages from the potentiometers 210, 212 and 214 to produce one or more reference signals of varying signal levels. Each of the reference signals are compared to the inverted flaw signal via designated comparators 224, 226 and 228 in the comparison circuit 202. When the inverted flaw signal falls below any of the reference signals, the appropriate light emitting diode (LED) 230, 232 and 234 is activated.

Additionally, a short pulse signal is emitted from the comparator and may be transmitted to further electrical control circuitry 236, such as a computer. Monostable multivibrators 238, 240 and 242 may be provided to condition the short pulse signal for proper input into the electrical control circuitry 236. Preferably, the multivibrators 238, 240 and 242 are adjustable between 1 microsecond and 500 milliseconds.

The operation of positioning means will now be described with reference to FIG. 3. The photocells 109a and 109b shown in FIG. 1A are positioned at each end of the spatial filter 108. Each of the photocells 109a and 109b generate output signals representative of the intensity of the incident light. Consequently, for an optical fiber positioned at the center of the beam, the output signals of the photocells 109a and 109b are equal. Any difference between the two output signals thus indicates that the optical fiber 102 is off center.

The output of photocells 109a and 109b are amplified by a pair of gain amplifiers 300 and 302. The difference between the amplified outputs is determined and amplified by a differential amplifier 304. The differential output of the differential amplifier 304 is compared to a predetermined positive voltage, shown as a +2.5 V, and a predetermined negative voltage, shown as a −2.5 V, by a pair of comparator circuits 306 and 308. In response to the outputs of the comparator circuits 306 and 308, light emitting diodes 310, 312 and 314 indicate that the optical fiber is either right of center, on center or left of center, respectively.

It should be understood that the above described circuits are comprised of conventional circuit elements which one skilled in the art could produce based on the disclosure herein and general knowledge in the art. In addition, other suitable combinations of circuit elements which may be implemented in the fiber optic flaw detector system 100 will be readily contemplated by those skilled in the art and should be considered within the scope of the invention.

Figure 1A:
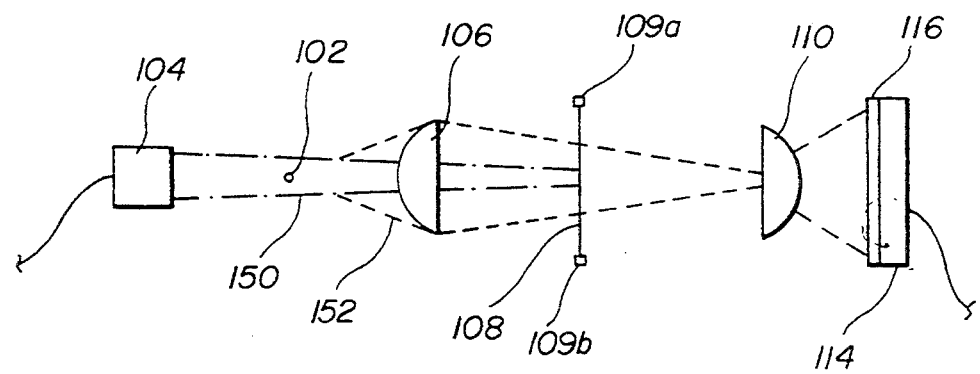
FIG. 1A is a schematic side view of the fiber optic flaw detector system of FIG. 1 showing the path of the beam.
Figure 1B:
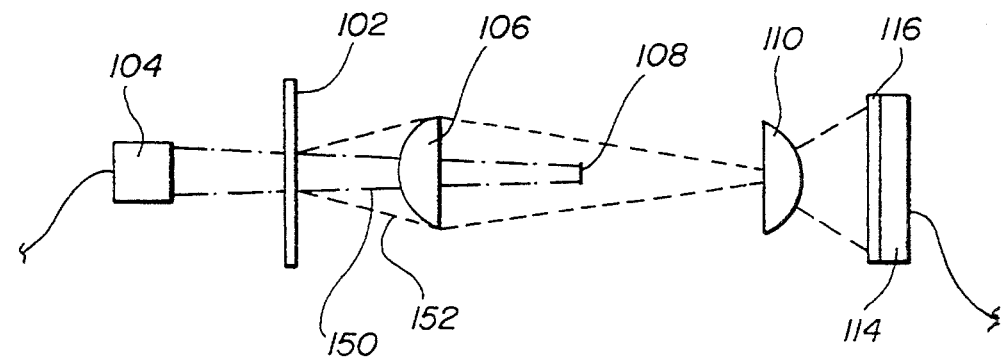
FIG. 1B is a schematic top view of the fiber optic flaw detector system of FIG. 1 showing the path of the beam.

An apparatus 134 for calibrating the fiber optic flaw detector system 100 is shown in FIGS. 1 and 1C. The apparatus 134 includes a cartridge 136 and an optical test fiber 138 having a known flaw 139 mounted therein. The optical test fiber 138 is mounted on the cartridge 136 by means of any suitable device. The apparatus 134 further includes mounting means 140 for mounting to the fiber optic flaw system 100. As shown in FIG. 1, mounting means 140 may comprise the air wipe plate 122. A moveable carriage 142 which preferably consists of the pair of moveable slide assemblies 130, 132 is attached to mounting means 140.

The cartridge 136 is adapted to be fixedly positioned on the moveable carriage 142. Preferably, the moveable carriage 142 includes a plurality of mounting pins 144. The cartridge 136 defines a plurality of mounting apertures 146 each of which is adapted to receive a corresponding one of the mounting pins 144. The moveable carriage 142 translates such that the known flaw 139 in the optical test fiber 138 passes into and out of the beam during calibration of the system 100. The movement of the ball slide assemblies 130, 132 is indicated by arrows 148 and 150.

During calibration, the cartridge 136 is mounted on the ball slide assemblies 130, 132 and the known flaw 139 is moved into and out of the laser beam. Simultaneously, an operator adjusts the potentiometers 210, 212 and 214 until a designated one of the light emitting diodes 230, 232 and 234 begins to blink on and off as the known flaw 139 passes into and out of the beam. Two other optical test fibers having different diameter flaws can then be calibrated until each of the potentiometers 230, 232 and 234 are set.

Figure 4:
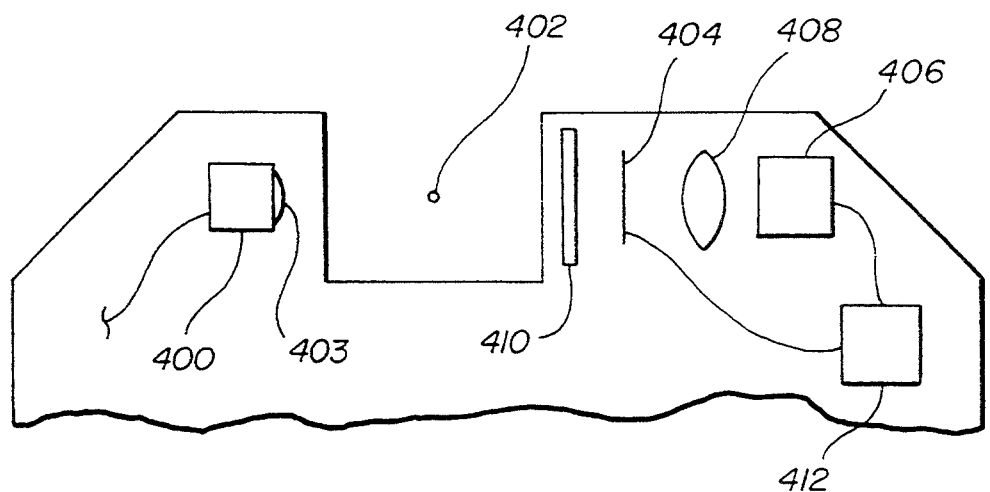
FIG. 4 is a schematic cross-sectional side view of a system for detecting flaws in an optical fiber which employs a linear light detector in accordance with a second embodiment of the present invention.

An alternative embodiment of the fiber optic flaw detector system will now be described with reference to FIG. 4. Laser beam generating means, such as a laser diode 400, generates a laser beam of collimated light rays which illuminate an optical fiber 402 substantially orthogonal to its longitudinal axis. A laser lens assembly 403 preferably focuses the laser beam into the optical fiber 402. As noted above, the optical fiber 402 scatters the laser beam into an in-plane scattered segment consisting of light rays which are scattered in a radial plane perpendicular to the longitudinal axis of the optical fiber 402 and an out-of-plane scattered segment consisting of light rays scattered outside of the radial plane due to flaws in the optical fiber 402.

A linear light detector 404 is positioned to detect the in-plane scattered segment of the laser beam. The linear light detector 404 also detects any portion of the laser beam which may pass around the optical fiber 402. An in-plane signal is generated by the linear light detector 404 representative of the intensity of the incident light. Light detection means detects the out-of-plane scattered segment of the laser beam and generates a flaw signal representative of thereof. The light detection means may include a photodetector 406 which generates the flaw signal in response to the out-of-plane scattered segment and a detector lens assembly, such as a biconvex lens 408, for focusing the out-of-plane scattered segment of the laser beam onto the photodetector 406. Preferably, a bandpass optical filter 410 receives the scattered laser beam from the optical fiber 402 before the linear light detector 404 to filter ambient ultraviolet light.

Figure 4A:
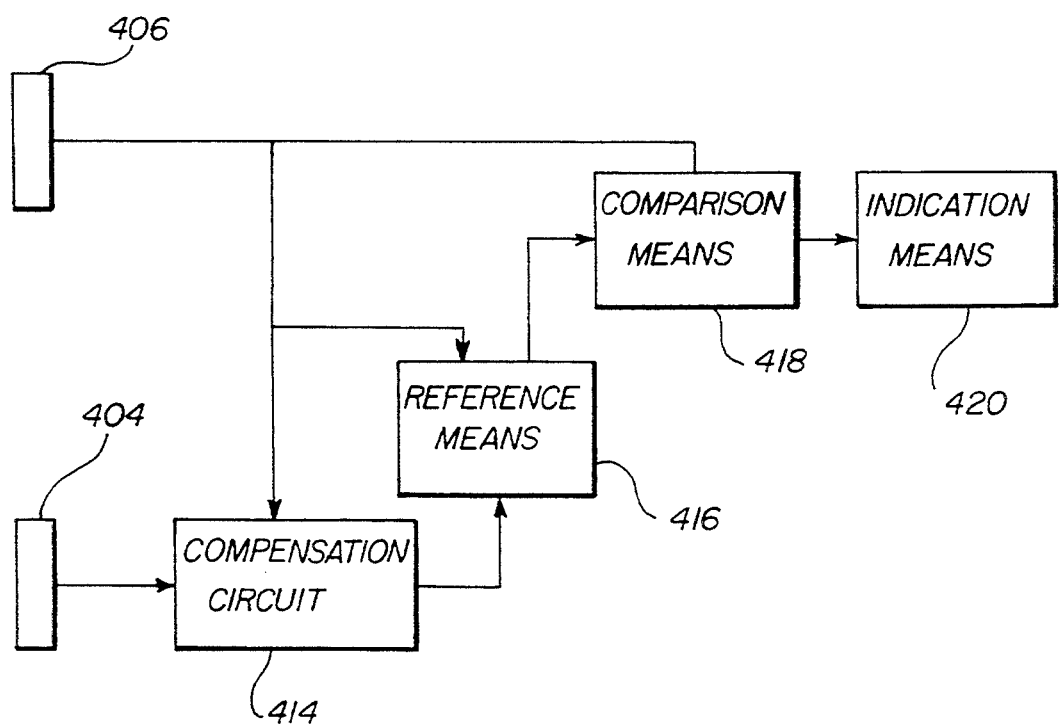
FIG. 4A is a schematic block diagram of an electrical circuit for determining the presence of a flaw using the fiber optic flaw detector system of FIG. 4.

The in-plane signal generated by the linear light detector 404 and the flaw signal generated by the photodetector 406 are transmitted to circuit means 412, as shown in FIG. 4A, which determines whether a flaw is present in the optical fiber 402. The circuit means 412 comprises a compensation circuit 414, reference means 416, comparison means 418 and indication means 420. The compensation circuit 414 receives the flaw signal and the in-plane signal and generates a compensation signal representative of any fluctuations in the total power of the laser beam. As is well known, fluctuations in the power of the laser beam may be caused by any number of factors including aging of the laser diode, changes in temperature and the like.

Reference means 416 sets at least one reference signal and modulates the reference signal based on the compensation signal from the compensation circuit 414. Comparison means 418 then compares the reference signal to the flaw signal to determine whether a flaw is present in the optical fiber 402. If a flaw is detected, comparison means 418 generates at least one comparison signal. Indication means 420 indicates the presence of the flaw in the optical fiber 402 in response to the comparison signal.

Having thus described the invention in detail by way of reference to preferred embodiments thereof, it will be apparent that other modifications and variations are possible without departing from the scope of the invention defined in the appended claims.

What is claimed is:

1. A system for detecting flaws in an optical fiber comprising:
a light source for generating a beam of collimated light rays, a first portion of said beam illuminating said optical fiber substantially orthogonal to a longitudinal axis thereof and a second portion of said beam passing around said optical fiber, said first portion of said beam being scattered by said optical fiber into an in-plane scattered segment consisting of light rays which are scattered in a radial plane substantially perpendicular to said longitudinal axis of said optical fiber and an out-of-plane scattered segment consisting of light rays which are scattered out of said radial plane, said out-of-plane scattered segment resulting from flaws in said optical fiber;

a light attenuator for substantially removing said in-plane scattered segment and said second portion of said beam, said light attenuator having first and second ends;

positioning means for detecting said beam mounted at said first and second ends of said light attenuator to determine the position of said optical fiber based on said beam and for indicating the position of said optical fiber;

a first lens assembly for focusing said second portion and said in-plane scattered segment of said beam onto said light attenuator;

a light detector in line with said light attenuator for detecting said out-of-plane scattered segment of said beam after said in-plane scattered segment and said second portion of said beam are substantially removed by said light attenuator and for producing a flaw signal representative thereof; and an electrical circuit for determining whether a flaw is present in said optical fiber in response to said flaw signal.

2. The fiber optic flaw detector system as recited in claim 1 wherein said light source comprises a laser beam generator.

3. The fiber optic flaw detector system as recited in claim 2 wherein said laser beam generator comprises a laser diode.

4. The fiber optic flaw detector system as recited in claim 1 wherein said light attenuator comprises a spatial filter for removing said in-plane scattered segment of said beam.

5. The fiber optic flaw detector system as recited in claim 1 wherein said first lens assembly comprises a plano-convex lens.

6. The fiber optic flaw detector system as recited in claim 5 further comprising a lens cleaner for providing a stream of air over said plano-convex lens to substantially continuously clean said plano-convex lens.

7. The fiber optic flaw detector system as recited in claim 6 wherein said lens cleaner comprises:
an air wipe plate adjacent said plano-convex lens for defining an air passage between said plate and said plano-convex lens, said plate defining a slot for transmitting said in-plane and out-of-plane scattered segments of said beam; and
an air source for producing air flow in said air passage to clean said plano-convex lens.

8. The fiber optic flaw detector system as recited in claim 1 wherein said light detector comprises a photodetector.

9. The fiber optic flaw detector system as recited in claim 8 wherein said light detector further comprises a bandpass optical filter for filtering ambient ultraviolet light, said bandpass optical filter being positioned to receive said out-of-plane scattered segment of said beam prior to receipt by said photodetector.

10. The fiber optic flaw detector system as recited in claim 9 further comprising a second lens assembly for focusing said out-of-plane scattered segment of said beam onto said bandpass optical filter and said photodetector.

11. The fiber optic flaw detector system as recited in claim 1 wherein said electrical circuit comprises:
a reference circuit for setting at least one reference signal based on said flaw signal;
a comparison circuit for comparing said flaw signal and said at least one reference signal to determine whether a flaw is present in said optical fiber and for generating at least one comparison signal representative thereof; and
an indicator circuit for indicating whether a flaw is present in said optical fiber in response to said at least one comparison signal.

12. The fiber optic flaw detector system as recited in claim 1 wherein said positioning means comprises:
a first photocell located on said first end of said light attenuator for receiving said beam and for generating a first position signal representative thereof;
a second photocell located on said second end of said light attenuator for receiving said beam and for generating a second position signal representative thereof; and
a position circuit for determining the position of said optical fiber based on said first and second position signals and for providing an indication of the position of said optical fiber.

13. A system for detecting flaws in an optical fiber comprising:
laser beam generating means for generating a laser beam of collimated light rays, said laser beam illuminating said optical fiber substantially orthogonal to a longitudinal axis thereof and being scattered by said optical fiber into an in-plane scattered segment consisting of light rays which are scattered in a radial plane substantially perpendicular to said longitudinal axis and an out-of-plane scattered segment consisting of light rays which are scattered out of said radial plane, said out-of-plane scattered segment resulting from flaws in said optical fiber;
a linear light detector for detecting said in-plane scattered segment of said laser beam and for generating an in-plane signal representative thereof;
light detection means for detecting said out-of-plane scattered segment of said laser beam and for producing a flaw signal representative thereof; and
circuit means for determining whether a flaw is present in said optical fiber in response to said flaw signal and said in-plane signal.

14. The fiber optic flaw detector system as recited in claim 13 comprising a bandpass optical filter for filtering ancient ultraviolet light, said optical filter being positioned to receive said in-plane and said out-of-plane scattered segments of said laser beam prior to receipt by said linear light detector.

15. The fiber optic flaw detector system as recited in claim 13 comprising a laser lens assembly for focusing said laser beam into said optical fiber.

16. The fiber optic flaw detector system as recited in claim 13 wherein said light detection means comprises:
a photodetector for detecting said out-of-plane scattered segment of said laser beam and for generating a flaw signal representative thereof; and
a detector lens assembly for focusing said out-of-plane scattered segment of said laser beam onto said photodetector.

17. The fiber optic flaw detector system as recited in claim 13 wherein said circuit means comprises:
a compensation circuit for generating a compensation signal representative of any fluctuation in the power of said laser beam based on said flaw signal and said in-plane signal;

reference means for setting at least one reference signal and for modulating said at least one reference signal based on said compensation signal;

comparison means for comparing said flaw signal and said at least one reference signal to determine whether a flaw is present in said optical fiber and for generating at least one comparison signal representative thereof; and indication means for indicating the presence of said flaw in said optical fiber in response to said at least one comparison signal.

18. An apparatus for calibrating a fiber optic flaw detector system which illuminates an optical fiber with a laser beam and includes a detection circuit for detecting scattering of said laser beam by said optical fiber to determine whether a flaw is present in said optical fiber, said apparatus comprising:

a cartridge;

an optical test fiber having a known flaw therein, said optical test fiber being mounted on said cartridge; and mounting means mounted on said flaw detector system and including a moveable carriage for removably mounting said cartridge on said mounting means, said moveable carriage being adapted to axially translate said optical test fiber such that said known flaw of said optical test fiber passes into and out of said laser beam to calibrate said fiber optic flaw detector system.

19. The apparatus as recited in claim 18 wherein said moveable carriage includes a plurality of mounting pins and said cartridge defines a plurality of mounting apertures each of which is adapted to receive a corresponding one of said plurality of mounting pins to removeably mount said cartridge on said moveable carriage.

20. The apparatus as recited in claim 19 wherein said moveable carriage comprises a pair of ball slide assemblies.

* * * * *

UNITED STATES PATENT AND TRADEMARK OFFICE
CERTIFICATE OF CORRECTION

PATENT NO. : 5,436,719
DATED : July 25, 1995
INVENTOR(S) : Joseph E. Doles, Robert J. Hadick It is certified that error appears in the above-indentified patent and that said Letters Patent is hereby corrected as shown below:

Col. 10, line 50 "ancient ultraviolet" should be --ambient ultraviolet--.

Signed and Sealed this

Fourteenth Day of November, 1995

Attest:

BRUCE LEHMAN

*Attesting Officer*     *Commissioner of Patents and Trademarks*